United States Patent
Matusch (10) Patent No.: US 9,427,526 B2
(45) Date of Patent: Aug. 30, 2016

(54) DISPOSABLE INJECTOR WITH A FLEXURALLY ELASTIC PISTON-ACTUATING RAM

(71) Applicant: Rudolf Matusch, Marburg (DE)

(72) Inventor: Rudolf Matusch, Marburg (DE)

(73) Assignee: LTS LOHMANN THERAPIE-SYSTEME AG, Andernach (DE)

(*) Notice: Subject to any disclaimer, the term of this patent is extended or adjusted under 35 U.S.C. 154(b) by 599 days.

(21) Appl. No.: 13/656,816

(22) Filed: Oct. 22, 2012

(65) Prior Publication Data

US 2014/0005611 A1 Jan. 2, 2014

Related U.S. Application Data

(63) Continuation-in-part of application No. PCT/EP2011/001842, filed on Apr. 13, 2011.

(30) Foreign Application Priority Data

Apr. 27, 2010 (DE) .................. 10 2010 018 529

(51) Int. Cl.
*A61M 5/20* (2006.01)
*A61M 5/30* (2006.01)
*A61M 5/50* (2006.01)
*A61M 5/31* (2006.01)

(52) U.S. Cl.
CPC ............. *A61M 5/30* (2013.01); *A61M 5/2033* (2013.01); *A61M 5/5086* (2013.01); *A61M 2005/2073* (2013.01); *A61M 2005/3104* (2013.01)

(58) Field of Classification Search
CPC ........... A61M 5/315; A61M 5/31501; A61M 5/31511; A61M 5/30; A61M 5/2033; A61M 2005/2073; A61M 5/20; A61M 2005/2026; A61M 2005/2006

USPC .................. 604/68, 136, 187, 218, 220, 228
See application file for complete search history.

(56) References Cited

U.S. PATENT DOCUMENTS

| | | | |
|---|---|---|---|
| 4,553,962 A | 11/1985 | Brunet | |
| 4,677,980 A * | 7/1987 | Reilly et al. | 600/432 |
| 4,961,728 A * | 10/1990 | Kosinski | 604/110 |
| 8,092,419 B2 | 1/2012 | Matusch | |
| 8,105,271 B2 | 1/2012 | Matusch | |
| 2007/0017532 A1* | 1/2007 | Wyrick | 128/898 |
| 2008/0077083 A1* | 3/2008 | Griffiths et al. | 604/85 |
| 2009/0254036 A1 | 10/2009 | Asmussen | |

FOREIGN PATENT DOCUMENTS

| | | | |
|---|---|---|---|
| DE | 84 901 A | 1/1896 | |
| WO | WO 2007/002052 | 1/2007 | |
| WO | WO 2007131025 A1 * | 11/2007 | A61M 5/2033 |

* cited by examiner

*Primary Examiner* — Edelmira Bosques
*Assistant Examiner* — Leah Swanson
(74) *Attorney, Agent, or Firm* — R. S. Lombard

(57) ABSTRACT

A disposable injector with a cylinder/piston unit that can be filled at least temporarily with active substance, with a housing in which a pretensioned and releasable mechanical spring energy reservoir is arranged, and with at least one piston-actuating ram positioned between the spring energy reservoir and the piston of the cylinder/piston unit. The piston-actuating ram has two draw hooks that engage around the housing in some areas. In addition, the piston-actuating ram is separable from the housing by the relaxing spring energy reservoir. With the present invention, a disposable injector is developed which, with a small overall size, comprises only a small number of components and, while being easy to handle, ensures safe storage and operation.

14 Claims, 5 Drawing Sheets

DISPOSABLE INJECTOR WITH A FLEXURALLY ELASTIC PISTON-ACTUATING RAM

CROSS-REFERENCE TO RELATED APPLICATION

This is a continuation-in-part application of pending international application PCT/EP2011/001842 filed Apr. 13, 2011 and claiming the priority of German Application No. 10 2010 018 529.9 filed Apr. 27, 2010.

BACKGROUND OF THE INVENTION

The invention relates to a disposable Injector with a cylinder/piston unit that can be filled at least temporarily with active substance, with a housing in which a pretensioned and releasable mechanical spring energy reservoir is arranged, and with at least one piston-actuating ram positioned between the spring energy reservoir and the piston of the cylinder/piston unit.

Such an injector is disclosed in U.S. Pat. No. 8,105,271 B2 issued Jan. 31, 2012 to the present assignee.

DE 10 2007 031 630 A1 discloses, among other things, an injector of this type. With the exception of the mechanical spring of the spring energy reservoir, almost all the components of the injector are produced expensively from plastics by injection moulding. Components that are subject to high mechanical loads are additionally reinforced with glass fibres.

Therefore, the problem addressed by the present invention is that of developing a disposable injector of modular design which, with a small overall size, comprises only a small number of components and, while being easy to handle and inexpensive to produce, ensures safe storage and operation.

SUMMARY OF THE INVENTION

This problem is solved by the features of the main claim. Accordingly, the piston-actuating ram has two draw hooks that engage around the housing in some areas. In addition, the piston-actuating rangy is separable the housing by means of the relaxing spring energy reservoir.

BRIEF DESCRIPTION OF THE DRAWINGS

Further details of the invention will become clear from the following descriptions of a number of illustrative embodiments represented schematically in the drawings, in which.

DETAILED DESCRIPTION OF THE PARTICULAR EMBODIMENTS

Figure 1:
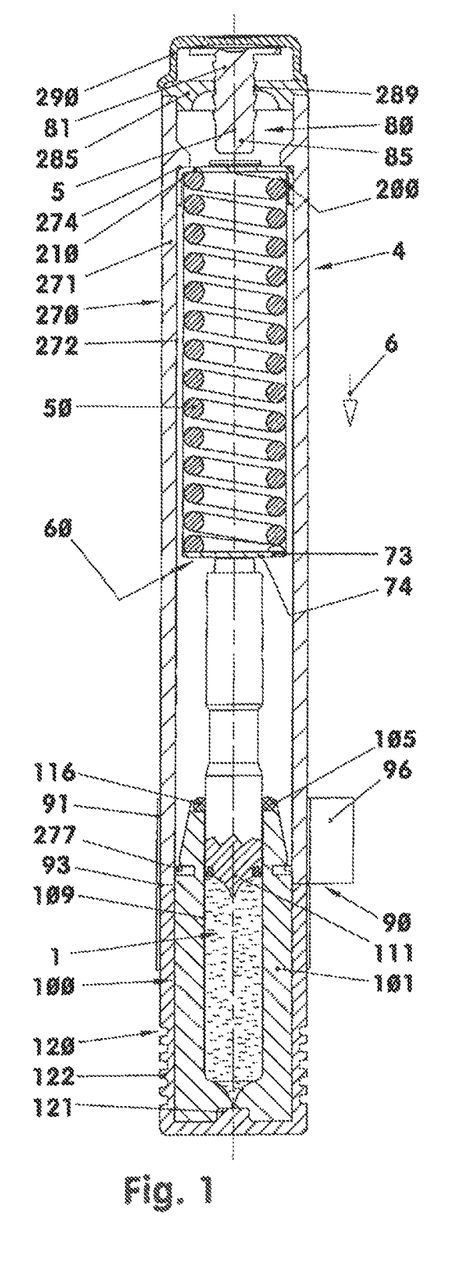
FIG. 1 shows a disposable injector.
Figure 2:
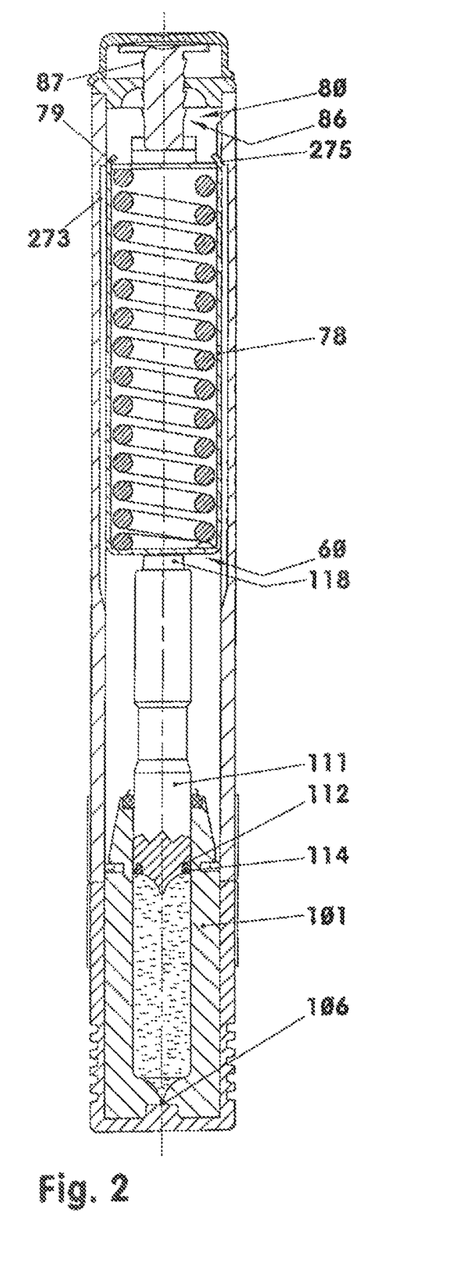
FIG. 2 shows the same as FIG. 1, but pivoted through 90 degrees.
Figure 3:
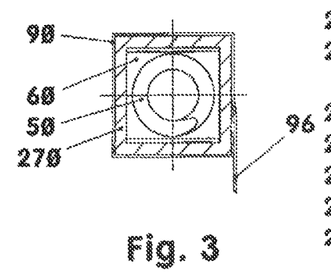
FIG. 3 shows a cross section of FIG. 2.

FIGS. 1 to 3 show a disposable injector (4) with a permanently charged spring energy reservoir (50). The disposable injector (4) comprises a jacket housing (270), which accommodates an inner housing (200), a piston-actuating ram (60), a helical compression spring (50) as spring energy reservoir (50), and a cylinder/piston unit (100). The cylinder/piston unit (100) sits for the most part in a protective cap (120).

The sleeve-shape jacket housing (270) comprises a tube part (271) of square cross section and a cover (285). The for example substantially smooth circumferential surface of the tube part (271) can bear embossed or affixed labels, inscriptions, etc. The inner wall (272) has, for example, release grooves (273) lying opposite one another. In the illustrative embodiment, these release grooves (273) are half as long as the tube part (271). In the view in FIG. 2, the upper and for example sharp-edged end of the release grooves (273) lies three millimeters below the upper end of the piston-actuating ram (60). Above the release grooves (273), the inner wall forms blocking surfaces (275), on which the piston-actuating ram (60) bears.

The cover (285), which can be integrally moulded on the square tube (271), holds the trigger unit (80) in a for example central bore (289). This trigger unit (80) comprises a manually activatable, for example mushroom-shaped trigger (81) with a loss prevention mechanism (86). In the illustrative embodiment, the loss prevention mechanism (86) is formed by locking wedges (87) or locking hooks which are arranged in an offset manner on the circumferential surface of the trigger ram (85) and which engage behind the inner face of the cover (285) or an undercut surface of the jacket tube (271). Runners are also conceivable instead of barbs. The trigger unit (80) is covered by a protective cap (290). If appropriate, an additional locking mechanism can be provided to prevent accidental actuation.

Figure 4:
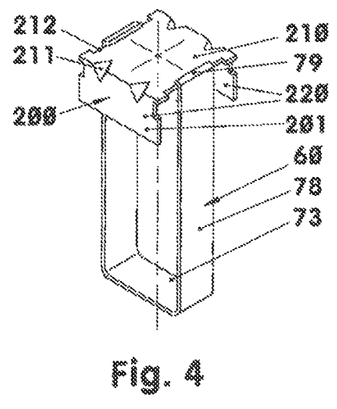
FIG. 4 shows a housing with piston-actuating ram.

The inner housing (200) is a sheet-metal strip (201) that has been bent to form a first "U" (cf. FIG. 4). The angled sheet-metal strip (201), having a width of 18 millimeters for example, is approximately 50 millimeters long. The sheet-metal strip (201), produced if appropriate from spring steel, has a wall thickness of 0.5 millimeter, for example. The bent sheet-metal strip (201) is composed of a central end plate (210) and of two arms (220) protruding at least approximately perpendicularly from the latter. The sheet-metal strip (201) has no bores or apertures passing through the center thereof and can therefore be produced substantially by means of simple cutting and forming steps.

At the transitions between the end plate (210) and the arms (220), two stiffening beads (211) are in each case pressed in according to FIG. 4. The stiffening beads (211) protrude so far into the end plate (210) that they additionally centre the last winding of the helical compression spring (50) on the end plate (210).

The piston-actuating ram (60) is a sheet-metal strip that has been bent in a U-shape and that is composed of a middle part, the ram plate (73), and two guide arms (78). In the illustrative embodiment, the piston-actuating ram (60) has no bores or apertures. It can therefore be produced by means of inexpensive bending and/or edging operations. The ram plate (73) is oriented parallel to the end plate (210). The flexurally elastic guide arms (78) protrude upwards at a right angle. The helical compression spring (50) sits between the guide arms (78). If appropriate, the guide arms (78) are stiffened relative to the ram plate (73) by stiffening beads, cf. the stiffening beads (211) of the sheet-metal strip (201).

At their upper end, the two guide arms (78) have angled collars (79), cf. FIGS. 2 and 4. These collars (79) enclose an angle of 135 degrees with the guide arms (78) for example. The enclosed angle can be, for example, between 100 degrees and 170 degrees. The collars (79) engage around and/or behind the end plate (210) in some areas, such that, in the view according to FIGS. 2 and 4, the piston-actuating ram (60) hangs from the housing (200).

According to FIG. 1, the piston-actuating ram (60) has a width that is slightly smaller, that is to say by ca. 0.1 to 0.3 millimeter, than the normal distance between the two arms (220). In FIG. 2, it will be seen that the guide arms (78) with the hooks (79) of the piston-actuating ram (60) bear only via the upper three millimeters on the inner wall (272) and/or the blocking surfaces (275) of the jacket housing (270). As soon as this distance has been travelled upon triggering, the hooks (79) spring into the release grooves (273), such that the spring (50) drives the ram plate (73) forwards.

The ram plate (73) can have a central bore for additionally guiding the rear end of the piston (111), then provided with a pin, of the cylinder/piston unit (100).

The housing (200) made from sheet metal is for the most part surrounded by the jacket housing (270) in which it sits and is able to slide. The jacket tube (271) made of metal, e.g. aluminium, or of plastic, e.g. a polyimide, has a wall thickness of 1.5 to 2.5 millimeters for example. In its rear area it has an assembly stop (274).

In the illustrative embodiment, the cylinder/piston unit (100) comprises a transparent cylinder (101) which is filled with an injection solution (1) or a solvent, e.g. water for injection, and in which, according to FIGS. 1 and 2, the piston (111) sits in its rear position.

The cylinder (101) is, for example, a thick-walled pot. The cylinder bore is, for example, cylindrical or frustoconical. In the centre of the bore, of which the cylinder base is adapted at least approximately to the contour of the front end face of the piston (111), there is a short cylindrical, nozzle-like bore (106). The diameter thereof is approximately 0.1 to 0.5 millimeter. This bore (106) is one to five times as long as its diameter. It ends in a cylindrical recess (107) in the outer end face (103) at the bottom of the cylinder (101), cf. FIG. 6. If appropriate, it is also possible to arrange two or more nozzle-like bores (106) in the base of the cylinder (101).

Around the recess (107), an adhesive ring (108) firmly adheres to the end face (103). The adhesive ring (108) covers almost the whole of the end face (103).

The spatial outer contour of the cylinder (101) has, for example, a square configuration in the illustrative embodiment. However, it can also be cylindrical. In the central area of the cylinder, the cross section of the outer contour, oriented transversely with respect to the centre line (5), is a square surface with a central bore.

In the upper quarter directed towards the square tube (270), the cylinder (101) has, in its outer contour, a for example circumferential retaining notch (104) with, for example, a rectangular notch cross section. Above the retaining notch (104), the cylinder (101) narrows in a truncated pyramid shape. The angle enclosed by mutually opposite pyramidal surfaces is, for example, 20 to 30 degrees. If appropriate, the retaining notch (104) can also be composed simply of two mutually opposite single notches.

The cylinder (101) has a cylinder inner wall (109) which, in the area of the rear end face of the cylinder, ends in an annular groove (105) for receiving a sealing element (116).

At its front and at least approximately conically shaped end face, the piston (111) lying in the cylinder (101) has an axial annular groove (112) for receiving a sealing ring (114) or a permanently elastic sealing compound. In its central area, the piston (111) has a waist, and, at its rear end, a central frustoconical pin (118). The piston (111) and the sealing element (116) and also the stopper (121) close the filled interior (110) of the cylinder in a sterile manner.

In the views in FIGS. 1 and 2, a pot-shaped protective cap (120) is fitted onto the cylinder (101) from underneath. The one-piece protective cap (120), which from the geometrical point of view is composed in principle of five plane walls, encloses the cylinder (101) laterally with slight play. The upper and, for example, plane end face of the protective cap (120) makes contact with the front end face of the square-shaped jacket housing (270). The outer wall of the protective cap (120) is profiled or structured so as to make it easier to pull off from the cylinder (101). In the illustrative embodiment, a groove profile (122) is used.

Figure 6:
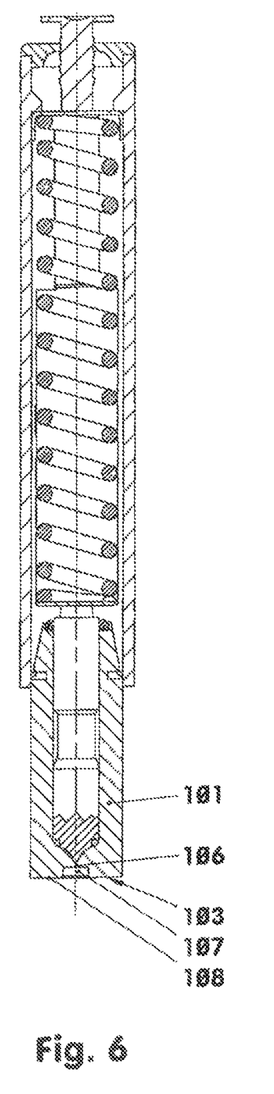
FIG. 6 shows the same as FIG. 1, but in the state when released and actuated.
Figure 7:
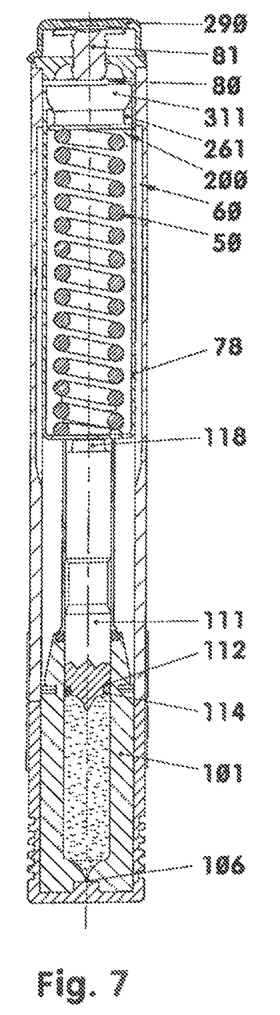
FIG. 7 shows a disposable injector with alternative trigger unit.

The base of the protective cap (120) has a stopper (121) which engages sealingly in the recess (107) of the cylinder (101), cf. FIGS. 1 and 6. The protective cap (120) adheres to the cylinder (101) via the adhesive ring (108). The latter has a substantially greater adherence to the cylinder (101) than it has to the base of the protective cap (120). In order to further ensure the difference in adherence, the base is optionally provided with a profile or a shoulder, such that the contact surface to the adhesive ring (108) is smaller than the contact surface between the adhesive ring (108) and the end face (103) of the cylinder.

The helical compression spring (50) sits pretensioned between the ram plate (73) and the end plate (210) of the sheet-metal strip (201). The spring force which, for example, is 500 Newton in the tensioned state, is transmitted via the ram plate (73) to the draw hooks (78) engaging behind the end plate (210)

According to FIGS. 1 and 2, the contact area of the square-shaped jacket tube (271) and the protective cap (120) is closed with a tamper-evident seal, e.g. a banderole (90) as safety element. The banderole (90), which can be torn off or separated, is, for example, a paper strip or film strip that is coated on one side with an adhesive. The film strip surrounds once, for example in a single layer, the combination of jacket housing (270) and protective cap (120). It temporarily affixes the parts (270) and (120). To prime the injector or remove the protective cap (120), in preparation for using the injector, the banderole (90) is pulled off or separated in such a way that the adhesive connection between the jacket tube (270) and the protective cap (120) is undone. For this purpose, in the illustrative embodiment, the tear-off tab (96) lying in the area of the jacket housing (270) is gripped and the banderole (90) is thus wound off, e.g. in sections. In doing so, the banderole (90) tears at a defined and, for example, rectilinear predetermined break point (93), which lies exactly in the area of the end faces. Consequently, during priming, only that part (91) of the banderole (90) bearing on the jacket housing (270) is removed.

Figure 5:
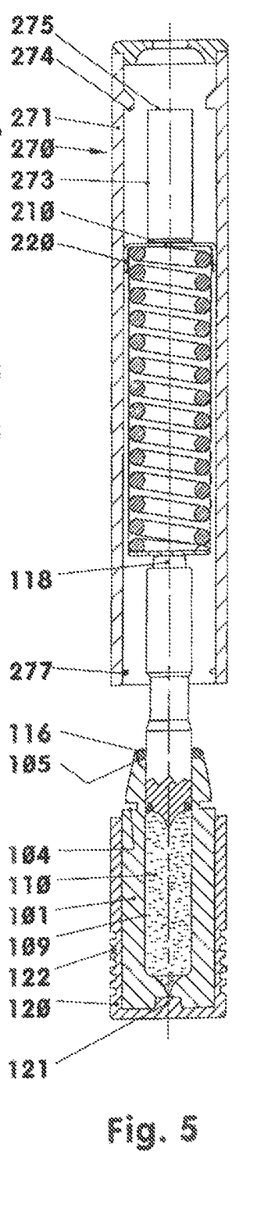
FIG. 5 shows a disposable injector in an intermediate stage of assembly.

FIG. 5 shows the injector (4) in an intermediate stage of assembly. The assembly procedure first entails joining the helical compression spring (50) to the piston-actuating ram (60) and to the sheet-metal strip (201). To do so, the helical compression spring (50) is fitted into the already shaped sheet-metal strip (201) in such a way that one end of the spring comes to bear on the end plate (210). The stirrup-like piston-actuating ram (60) is pushed onto the other end of the spring. Then, with the aid of an assembly device that guides the helical compression spring (50) on the outside or inside, the sheet-metal strip (201) is pushed together between the end plate (210) and the piston-actuating ram (60), counter to the spring action, to such an extent that the collars (79) lock on the end plate (210).

The combination of the tensioned spring (50), of the sheet-metal strip (201) and of the piston-actuating ram (60), still tensioned in the assembly device, is now inserted from underneath into the jacket housing (270).

The end plate (210) is pushed forward as far as the assembly stop (274). The hooks (79) are then blocked by the blocking surfaces (275). The assembly tool can now be removed. The spring (50) is blocked and cannot trigger.

In a further assembly stage, the filled cylinder/piston unit (100) is inserted, with the guide pin (118) of the piston (111) to the front, into the square tube (270). The locking elements (277) of the jacket housing (270) engage firmly in the retaining notch (104) and thus fix the cylinder/piston unit (100) in the square tube (270). The blocking surfaces (275) bearing on the piston-actuating ram (60) secure the latter in a stable position. In the assembly stage shown in FIG. 1, all that remains to be done is for the tamper-evident seal (90) to be applied.

To prepare for the use of the disposable injector shown in FIGS. 1 to 6, the tear-off tab (96) and the rear banderole section (91) are first of all torn off. The protective cap (120) is then withdrawn from the cylinder/piston unit (100). The injector, with the adhesive ring (108) to the front, is then positioned on the injection site. The disposable injector (4) is held in the first by the square tube (270). The thumb of the hand holding it lies, for example, on the trigger (81), e.g. as when holding a pen.

The trigger element (81) is now moved in the direction of the cylinder/piston unit (100). The trigger ram (85) moves the inner housing (200) relative to the jacket housing (270). If appropriate, the trigger element (81) engages with other locking wedges (87) in the cover (285). The guide arms (78) of the piston-actuating ram (60) slide, with their bearing surface decreasing, downwards along the blocking surfaces (275). As soon as the guide arms (78) no longer bear on the blocking surfaces (275), the stable securing is detached. The spring (50) supported on the housing (200) and acting on the ram plate (73) presses the piston-actuating ram (60) downwards. In doing so, the collars (79) disengage from the locking state with the end plate (210) and into the release grooves (273). The piston-actuating ram (60) is detached from the inner housing (200) and freed. The inner housing (200) is, for example, thrown back against the assembly stop (274). The end face (74) of the ram plate (73) strikes the end face of the piston (111), which has hitherto been situated about three millimeters away. The piston (111) forces the injection solution or the medicament (1) through the nozzle (106), e.g. initially at $200 \times 10^5$ Pa, until the cylinder (101) is emptied, cf. FIG. 6. The injection procedure is completed with the discharging of the injection solution (I).

FIGS. 7-11 show a disposable injector (4) that differs from the previously described injector in terms of the structure of the trigger unit (80) and in terms of the structure of the housing (200). The cylinder/piston unit (100) is configured as has been described in connection with the first illustrative embodiment.

The housing (200) has two long and wide arms (220), of which the free ends are each bent at an angle of 90 degrees for example. There, they form retaining elements (221) which are, for example, between 1.5 and 3 millimeters long, point towards each other and are oriented in a plane parallel to the end plate (210). Instead of the hook-shaped retaining element (221), each arm (220) can be provided with a recess in which the cylinder of the cylinder/piston unit (100) can be suspended in each case by means of a pin.

The piston-actuating ram (60) is of a similar structure to the piston-actuating ram (60) described in connection with the first illustrative embodiment. The hooks (79) protruding upwards above the housing (200) in FIGS. 7-9 comprise tabs (261) bent off on both sides. Each of these tabs (261) has a locking surface (262) engaging behind the end plate (210) and a guide surface (263) oriented in the direction of the trigger (81), cf. FIG. 10. In the illustrative embodiment, the planes of both surfaces (262, 263) enclose an angle of 60 degrees. The individual locking surface (262) and the associated long arm (266) of the draw hook (78) area for example, at right angles to each other.

Each of the locking surfaces (262) is adjoined by a slide surface (264) directed away from the long arms (266) of the guide arms (78). In the illustrative embodiment, the two said surfaces (262, 264) enclose an angle of 135 degrees.

The trigger unit (80) comprises a trigger element (81) and a trigger disc (311). The for example mushroom-shaped trigger element (81) protrudes with the trigger ram (85) into the cover (285). The locking hooks (87) engaging behind the cover (285) avoid the trigger element (81) falling out of the cover (285).

In the illustrative embodiment, the trigger disc (311) lies loosely in the jacket housing (270) above the housing (200). At its periphery, it is centred on the inner wall (272) of the square tube (270), for example by means of four centring lugs (312). According to the view in FIG. 10, the trigger disc (311) has insertion surfaces (313) which, at least with the trigger unit (80) actuated, ear on the guide surfaces (263) of the piston-actuating ram (60).

Figures 11, 12, 13, 14:
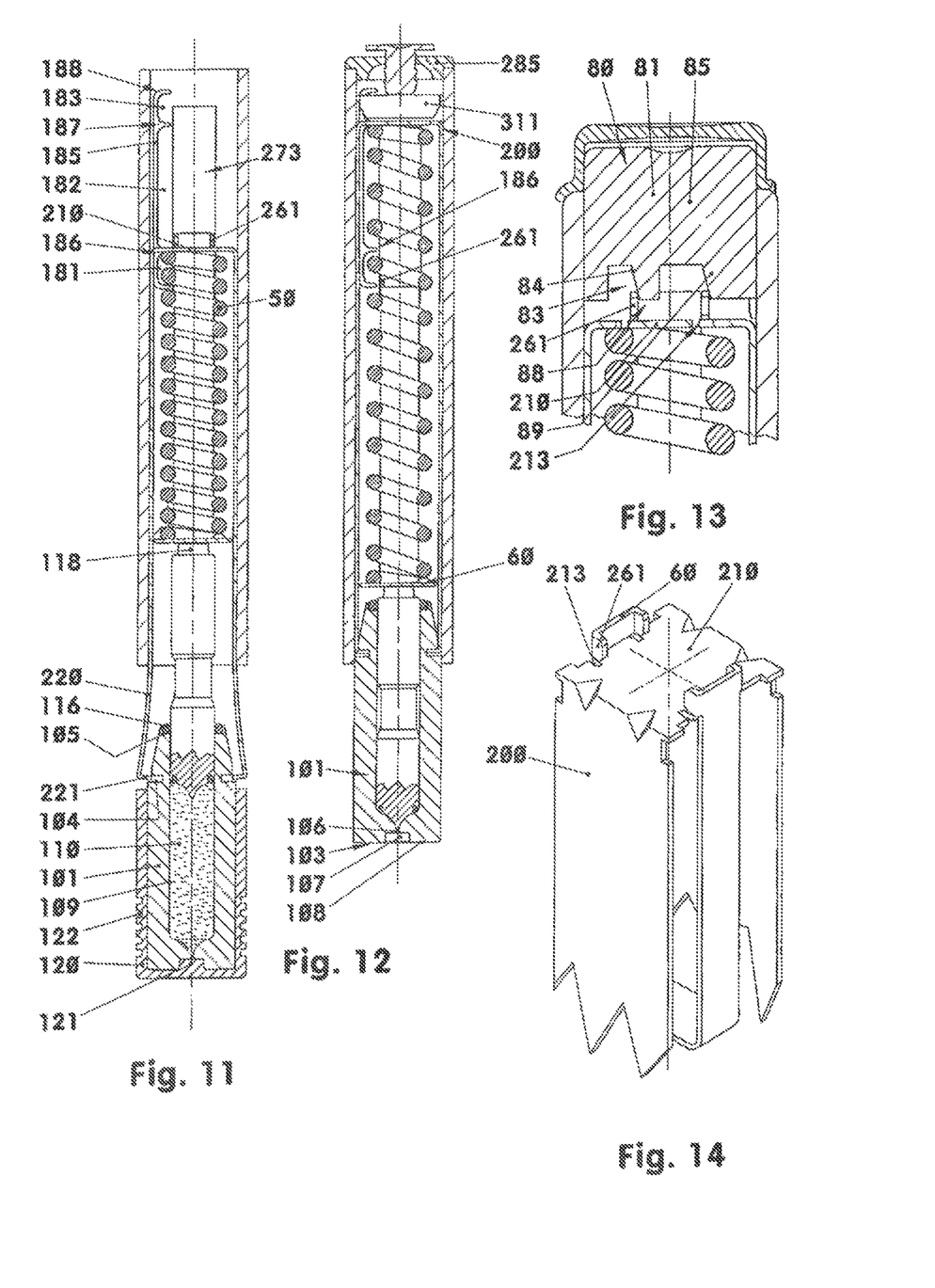
FIG. 11 shows an intermediate stage of assembly.
FIG. 12 shows the same as FIG. 7, but in the state when released and actuated.
FIG. 13 shows a disposable injector with trigger unit tubes of constant inner cross section.
FIG. 14 shows a housing and ram from FIG. 13.

In the rear area of the square tube (270), three elastic locking tabs (181-183) are arranged protruding several tenths of a millimeter inwards, cf. FIGS. 11 and 12. The locking tabs (181-183) each have a rectangular shape, for example. Their wall thickness corresponds to ca. 50% of the wall thickness of the square tube (270). On three sides they adjoin the wall of the square tube (270) and the nearest locking tab via gaps (185). The gaps (185) have a width of 0.5 millimeter, for example. The width corresponds to the wall thickness of the end plate (210). At the locations where two gaps (185) abut each other at right angles, the locking tabs (181-183) are rounded.

The eccentrically arranged locking tabs (181-183) formed integrally on the square tube secure the position of the sheet-metal strip (201) at three locations (186-188). For this purpose, they protrude several tenths of a millimeter into the interior of the trigger element (81). The first location (186) is the gap between the front locking tab (181) and the middle locking tab (182). In the gap which is horizontal there, the end plate (210) is locked (cf. FIG. 11) when the sheet-metal strip (201), with the helical compression spring (50) tensioned between the piston actuating ram (60) and the end plate (210), is assembled for further intermediate storage.

The second location (187) is the gap between the middle locking tab (182) and the rear locking tab (183). According to FIGS. 7 and 12, the end plate (210) sits here in a fully assembled disposable injector before and after triggering. The locking of the end, plate (210) in this gap avoids the housing (200) falling out of the square tube (270) after the protective cap (120) has been removed. The third location (188) is the gap above the rear locking tab (183).

If appropriate, the upper corners of the locking tabs (181-183), i.e. the corners directed towards the cover (285), are designed with sharp edges, such that the sheet-metal strip (201) can only be pushed into the square tube (270). A movement in the opposite direction is then impossible FIG. 11 shows the injector in an intermediate stage of assembly. Analogously to the first illustrative embodiment, the housing (200) is first assembled with the spring (50) and the piston-actuating ram (60).

The combination of the tensioned spring (50), of the sheet-metal strip (201) and of the piston-actuating ram (60), still tensioned in the assembly device, is now inserted from underneath into the square tube (270). The insertion procedure finishes when the end plate (210) locks in the gap (186) situated between locking tabs (181) and (182). In this position (186), cf. FIG. 11, the free ends of the arms (220) protrude downwards from the square tube (270)

In a further assembly stage, the filled cylinder/piston unit (100) is inserted, with the guide pin (118) of the piston (111) to the front, into the square tube (270) in such a way that the retaining elements (221) of the arms (220) engage in the retaining notch (104) of the cylinder (101). Starting from this position, the square tube (270) is pushed further over the sheet-metal strip (201) until the end plate (210) locks in the gap (187) situated between the locking tabs (182) and (183). In this process, the retaining elements (221) engage securely in the retaining notch (104) and thus fix the cylinder/piston unit (100) in the square tube (270). The tamper-evident seal is then applied.

The housing (200) can be designed without arms (220) and/or without retaining elements (221). Assembly is then carried out in the manner described, in connection with the first illustrative embodiment. The ram plate (73) of the piston-actuating ram (60) can have a central bore for receiving the guide pin (118) of the piston (111).

Figure 8:
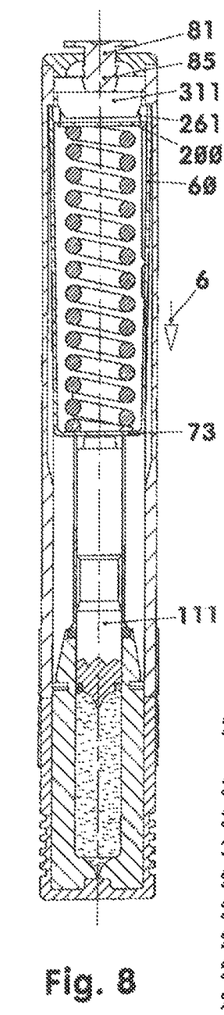
FIG. 8 shows the same as FIG. 7, but when triggered.
Figure 9:
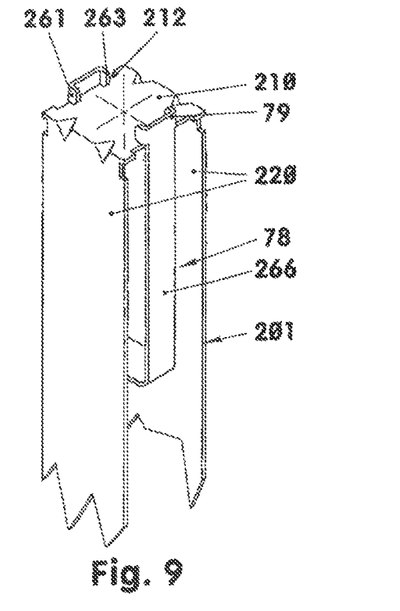
FIG. 9 shows a housing with piston-actuating ram.
Figure 10:
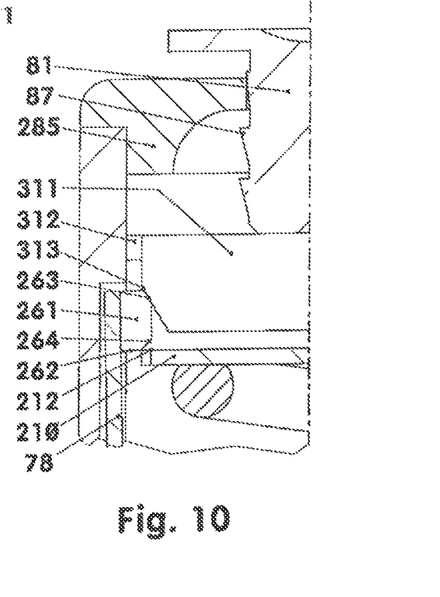
FIG. 10 shows a detail of the trigger unit from FIG. 8.

To trigger the disposable injector (4), the trigger (81) is actuated after removal of the tamper-evident seal (90) and withdrawal of the protective caps (120) and (290), Cf. FIGS. 8 and 10. The trigger ram (85) presses on the trigger disc (311), which acts with its insertion surfaces (313) on the guide surfaces (263). The guide surfaces (263) are forced apart until the slide surfaces (264) reach the edges (212) of the end plate (210).

The helical compression spring (50) acting on the end plate (210) and on the ram plate (73) pulls the tabs (261) away from the end plate (210) and thus separates the housing (200) from the piston-actuating ram (60). The piston-actuating ram (60) pushes the piston (111) in the direction of the nozzle (106), whereupon the injection solution (1) is ejected through the nozzle (106).

FIGS. 13 and 14 show details of a disposable Injector (4) whose trigger unit (80) comprises a wedge gear (83). The structure of the disposable injector (4) corresponds substantially to the structure of the injector (4) described in the preceding illustrative embodiment. However, the inner wall (272) of the jacket housing (270) has no release grooves (273). In the illustrative embodiment, the square tube (270) has a constant inner cross section along its length, all the inner surfaces being identical to one another. The inner cross section can also have a circular, octagonal, oval, etc., cross-sectional surface area. This disposable injector (4) has no cover (285).

In the illustrative embodiment, the end plate (210), which can be held by locking tabs (181-183) and gaps (185) (cf. FIG. 11), has four eccentric slits (213) For better illustration, FIG. 13 shows a partial detail of the end plate (210). The length and width of the individual slit (213) is greater than the corresponding dimensions of an individual tab (261). In the view in FIGS. 13 and 14, the piston-actuating ram (60) is configured in the same way as the piston-actuating ram (60) shown in FIGS. 7-12.

The trigger unit (80) comprises a trigger (81), guided, for example, in the jacket housing (270) and having a trigger ram (85). The latter has, for example, at least in some areas, a square cross-sectional surface area, which at the same time represents the maximum cross-sectional surface area of the trigger element (81). On its end face (88) directed towards the housing (200), the trigger ram (85) carries two wedges (89). The wedge surfaces (84), enclosing for example an angle of 15 degrees with respect to the longitudinal direction (5), bear on the tabs (261) of the piston-actuating ram (60).

When the trigger element (81) is actuated, the tabs 261) are moved to the left in the view in FIG. 13 by means of the wedge gear (83) on account of the small wedge angle, the operator only has to apply a slight force for this purpose. As soon as the tabs (261) are above the slits (213), the relaxing spring (50) pulls the tabs (261) down through the recesses (213). The piston-actuating ram (60) is separated from the housing (200) and pushes the piston (111) in the direction of the nozzle (106). By virtue of the long guide path of the non-protruding trigger element (81), there is no danger of tilting and no danger of the user getting a finger caught. In the illustrative embodiment, the size of the cross-sectional surface area defined by the envelope contours of the end plate (210) and of the draw hooks (78) remains constant during triggering and after triggering. However, the surface extent of said surface can also be reduced after triggering, depending of course on the pretensioning of the flexurally elastic guide arms (78)

Figure 15:
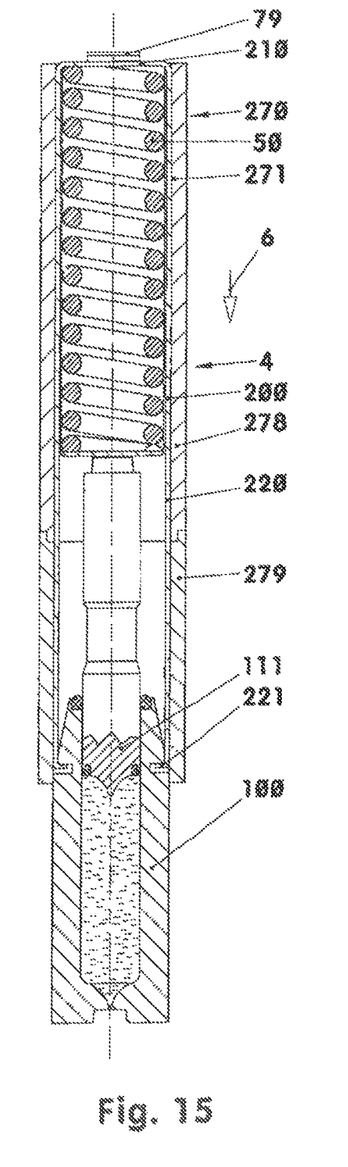
FIG. 15 shows a disposable injector with insert housing.
Figure 16:
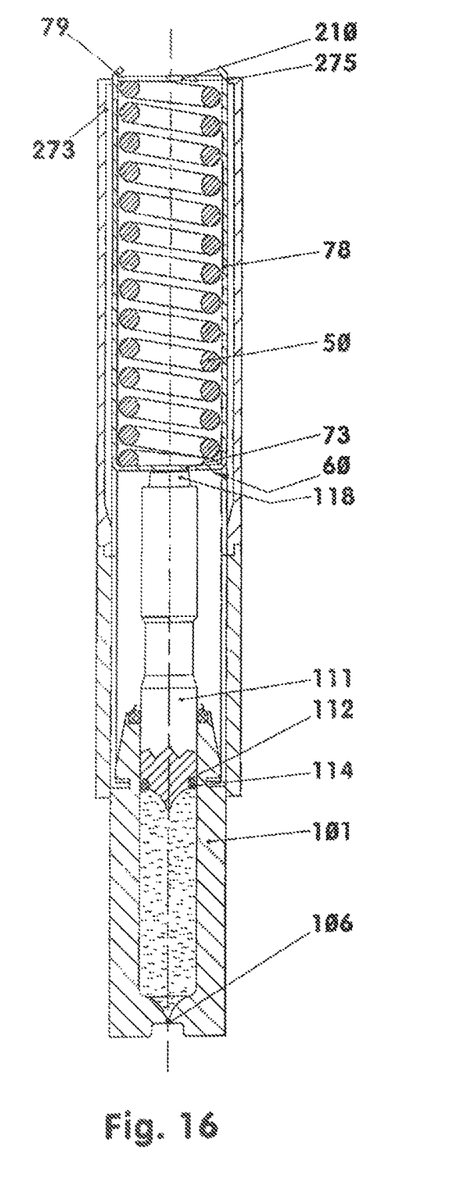
FIG. 16 shows the same as FIG. 15, but pivoted through 90 degrees.

FIGS. 15 and 16 show another disposable injector (4) with an insert housing. The piston-actuating ram (60) and the cylinder/piston unit (100) are configured as is described in connection with FIGS. 1-6. In contrast to the housing (200) shown in the latter, the housing (200) now has long arms (220) and retaining elements (221). These are designed as described in connection with FIGS. 7-12. The disposable injector (4) has no separate trigger element. The square tube (270) is designed in two parts. The length of the upper part (278) in this illustrative embodiment is about half the length of the tube part (271) shown in FIGS. 1-12. As in these illustrative embodiments, the jacket housing (270) has blocking surfaces (275) and release grooves (273). The blocking surfaces (275) here are, for example, two millimeters high. In the views in FIGS. 15 and 16, the protective cap (120) has been removed.

During assembly, the housing (200) with the spring (50) and with the piston-actuating ram (60) is inserted into the square tube (270) until the end plate (210) protrudes approximately 0.5 millimeter from the jacket tube (270). The hooks (79) then protrude by approximately one millimeter. After insertion of the cylinder/piston unit (100), the lower half (279) of the jacket tube (271) is pushed on and fixed. The retaining elements (221) are thus secured. The protective cap (120) is then fitted. After the tamper-evident seal (not shown here) has been applied, the injector (4) is packaged ready for use.

Before the disposable injector (4) is used, the tamper-evident seal is removed and the protective cap (120) withdrawn. The injector (4) is now picked up like a pen and placed onto the injection site. To trigger it, the user applies his thumb to the end plate (210) and presses the latter down by about two millimeters. The housing (200), with the piston-actuating ram (60) suspended therefrom, is pushed downwards relative to the jacket tube (270) in the views in FIGS. 15 and 16. Under the action of the spring (50), the hooks (79) leave the blocking surfaces (275) and spring into the release grooves (273). The spring (50) accelerates the piston-actuating ram (60) in the direction (6) of the triggering movement. For example, after the piston-actuating ram (60) has been released from the housing (200), it strikes the piston (111) initially spaced apart from the ram plate (73). The piston (111) is driven in the direction of the nozzle (106), whereupon the injection solution (1) is ejected.

The disposable injector (4) shown in FIGS. 15 and 16 is composed of only eight structural parts. These parts are the housing (200) the piston-actuating ram (60), the spring (50) two square tube sections (278, 279), a cylinder (101), a piston (111) and a protective cap (120).

Combinations of the various illustrative embodiments are also conceivable

LIST OF REFERENCE SIGNS 1 injection solution; medicament
4 disposable injector
5 centre line of injector, longitudinal direction
6 direction of triggering movement of (81), downward movement in direction of arrow
50 spring element, helical compression spring, spring energy reservoir
60 piston-actuating ram
73 ram plate
74 end face, lower
78 guide arm, draw hook
79 collars, hooks
80 trigger unit
81 trigger, trigger element
83 wedge gear
84 wedge surfaces
85 trigger ram
86 loss prevention mechanism
87 locking wedges, runners, locking hooks
88 end face
89 wedges
90 tamper-evident seal, banderole, safety element
91 rear banderole section, on (270); part
93 predetermined break point, perforation
96 tear-off tab
100 cylinder/piston unit
101 cylinder
103 end face
104 retaining notch
105 annular groove
106 bore, nozzle
107 recess in the end face
108 adhesive ring
109 inner wall of cylinder
110 interior of cylinder
111 piston
112 annular groove
114 sealing ring, seal
116 sealing element in (105)
118 guide pin
120 protective cap
121 stopper
122 groove profile
181 locking tab, front; locking element
182 locking tab, middle; locking element
183 locking tab, rear; locking element
185 gap
186 1st location
187 2nd location
188 3rd location
200 inner housing; sheet-metal part, thin-walled
201 sheet-metal strip; sheet-metal part
210 end plate
211 beads, stiffening beads
212 edges
213 slits, cutouts
220 arm
221 retaining elements
261 tabs
262 I locking surface
263 guide surface
264 slide surface
266 long arm of (78)
270 jacket housing, square tube
271 tube part, jacket tube
272 inner wall
273 release grooves
274 assembly stop
275 blocking surfaces
277 locking elements
278 upper part of (271)
279 lower part of (271)
285 cover
289 bore
290 protective cap
311 trigger disc
312 centring tugs
313 insertion surfaces

What is claimed is:

1. A disposable injector (4) including a cylinder/piston unit (100) including a cylinder (101) that can be filled at least temporarily with active substance in operative arrangement with a piston (111), an inner housing (200) in which a pretensioned and releasable helical compression spring (50) is arranged, and a piston-actuating rain (60) in operative arrangement with the helical compression spring (50) and the piston (111) of the cylinder/piston unit (100), an improvement of the disposable injector (4) comprises:
the piston-actuating rain (60) is U-shaped and consists of a middle rain plate (73) and two flexurally elastic draw hooks (78) oppositely disposed on opposite sides of the middle rain plate (73) that extend upwardly from the middle rain plate (73) and externally of the helical compression spring (50), each of the draw hooks (78) having at an end thereof an angled collar hook (79), each of the angled collar hooks (79) extends inwardly towards a centre line (5) of the disposable injector (4) in operative engagement with an end plate (210) of the inner housing (200) in some areas prior to actuation of the disposable injector (4), the end plate (210) has no bores or apertures passing through the center thereof, the helical compression spring (50) operatively disposed between the two flexurally elastic draw hooks (78) and above the middle rain plate (73) and below the end plate (210),
the piston-actuating rain (60) is separable from the inner housing (200) by means of releasing the helical compression spring (50), and
both the inner housing (200) and also the piston-actuating rain (60) are thin-walled sheet-metal parts.

2. The disposable injector (4) according to claim 1, wherein the inner housing (200) is surrounded by a jacket housing (270) that has a constant inner cross section along its length.

3. The disposable injector (4) according to claim 2, wherein the jacket housing (270) has an inner wall (272) having release grooves (273) therein of predetermined length for receiving the angled collar hooks (79) of the draw hooks (78) upon actuation of the injector (4).

4. The disposable injector (4) according to claim 3, wherein the jacket housing (270) includes a jacket tube (271) including an upper part (278) and a lower part (279), the lower part (279) including retaining elements (221) for retaining the cylinder/piston unit (100).

5. The disposable injector (4) according to claim 3, wherein the jacket housing has blocking surfaces (275) for maintaining the drawing hooks (78) in position prior to actuation of the injector (4).

6. The disposable injector (4) according to claim 1, wherein the piston-actuating rain (60) is a monolithic structure.

7. The disposable injector (4) according to claim 1, wherein each of the angled collar hooks (79) engages around or behind the end plate (210) in some areas prior to actuation of the disposable injector (4).

8. The disposable injector (4) according to claim 1, wherein each of the collar hooks (79) protrude upwards above the inner housing (200), the collar hooks (79) including tabs (261) bent off on both sides thereof.

9. The disposable injector (4) according to claim 8, further comprising a trigger unit (80) comprising a trigger (81) in operative arrangement with the jacket housing (270), the trigger unit (80) including a trigger rain (85).

10. The disposable injector (4) according to claim 9, wherein the end plate (210) has slits (213) in predetermined positions.

11. The disposable injector (4) according to claim 10, wherein the trigger rain (85) carries two wedges (89), each including a wedge gear (83) having a wedge surface (84) for bearing on one of the tabs (261), whereby the piston-actuating rain is separated from the end plate (210) upon the wedge gear (83) causing the tabs (261) to align and pass through the slits (213) during actuation of the injector (4).

12. The disposable injector (4) according to claim 9, wherein the trigger unit (80) further comprises a trigger disc (311) including insertion surfaces (313), the tabs (261) have guide surfaces (263), upon actuation of the trigger unit (80) the insertion surfaces (313) bear on the guide surfaces (261), whereby the piston-actuating rain (60) is separated from the inner housing (200).

13. The disposable injector (4) according to claim 1, wherein the middle rain plate (73) includes an end face (74) for striking a first-end of the piston (111) during actuation of the injector (4).

14. The disposable injector (4) according to claim 13, wherein the piston (111) has a guide pin (118) operatively centered at the first end of the piston (111).

\* \* \* \* \*